SELECTED 2-TRICHLOROMETHYL-4-PYRIMIDINYL CARBOXYLIC ESTERS AND THEIR USE AS FUNGICIDES

BACKGROUND OF THE INVENTION

1. Field of the Invention

This invention relates to selected 2-trichloromethyl-4-pyrimidinyl carboxylic esters and their use as fungicides.

2. Description of the Prior Art

British Pat. No. 1,181,657 discloses the use of 5,6-dimethyl-2-dimethylamino-4-pyrimidinyl dimethylcarbamate as an insecticide.

BRIEF SUMMARY OF THE INVENTION

Accordingly, the present invention is directed to, as compositions of matter, selected 2-trichloromethyl-4-pyrimidinyl carboxylic esters having the formula:

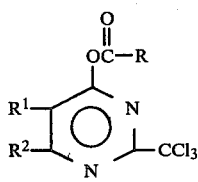

(I)

wherein R is a lower alkyl group having 1 to 4 carbon atoms, a lower alkenyl group having 1 to 4 carbon atoms, a lower halo alkyl group having 1 to 4 carbon atoms or an unsubstituted or substituted phenyl group; $R^1$ is hydrogen or halo; and $R^2$ is a lower alkyl group having 1 to 4 carbon atoms. It is to be understood that the term "halo" as used in the specification and claims herein is intended to include fluoro, chloro, bromo and iodo. The present invention is also directed to the use of these compounds as fungicides.

DETAILED DESCRIPTION

The carboxylic ester compounds of the present invention may be prepared by reacting trichloroacetamidine with a selected acetoacetate to form the corresponding 4-hydroxy-2-trichloromethylpyrimidine, which is then reacted with a selected carboxylic acid chloride. These general reactions are illustrated below in equations (A) and (B). In equation (A), trichloroacetamidine is reacted with ethyl 2-chloroacetoacetate to form 5-chloro-4-hydroxy-6-methyl-2-trichloromethyl-pyrimidine. In equation (B), the 5-chloro-4-hydroxy-6-methyl-2-trichloromethylpyrimidine is reacted with trichloroacetyl chloride to form 5-chloro-6-methyl-4-trichloroacetoxy-2-trichloromethylpyrimidine.

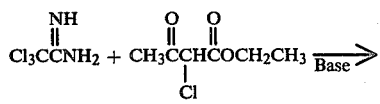

(A)

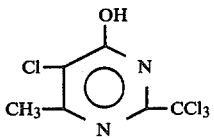

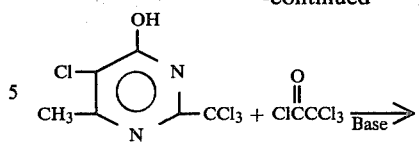

(B)

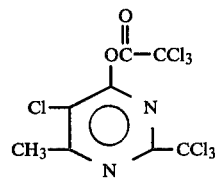

The trichloroacetamidine reactant is made by reacting trichloroacetonitrile with ammonia. Trichloroacetonitrile is a commercially available material. See German Pat. No. 671,785.

The acetoacetate reactants may be made by reacting the corresponding acetate with a suitable condensing agent such as sodium ethoxide. See Hickenbottom, W. J., *Reactions of Organic Compounds* (3rd Edition), pages 359 and 360 (1957). For example, ethyl acetate may be treated with sodium ethoxide, and the resulting mixture acidified to form ethyl acetoacetate. Various acetoacetates such as methyl acetoacetate and ethyl acetoacetate are commercially available.

Illustrative acetoacetate reactants for the compounds of the present invention include the following:
ethyl acetoacetate;
methyl acetoacetate;
ethyl 2-chloroacetoacetate;
ethyl buryrylacetate.

The carboxylic acid chloride reactants may be made by reacting the corresponding acid with thionyl chloride. See Patai, S., *The Chemistry of Acyl Halides*, pages 35–40 (1972). For example, trichloroacetic acid may be reacted with thionyl chloride to produce trichloroacetyl chloride. Various carboxylic acid chlorides such as trichloroacetyl chloride and 2-fluorobenzoyl chloride are commercially available.

Illustrative carboxylic acid chloride reactants for the compounds of the present invention include the following:
acetyl chloride;
crotonyl chloride;
trichloroacetyl chloride;
benzoyl chloride;
2-fluorobenzoyl chloride.

Any suitable conventional reaction conditions may be employed in the synthesis of the 4-hydroxy-2-trichloromethylpyrimidine compounds. See Henze et al., *J. Org. Chem.*, 17, 1320 (1952); Falch et al., *J. Med. Chem.*, 11, 608 (1968); and U.S. Pat. No. 3,118,889 as examples of such a synthesis.

A wide variety of conventional reaction conditions may be employed in the synthesis of the present compounds according to equation (B) and the present invention is not intended to be limited to any particular reaction conditions. For example, acylation of the hydroxyl group of the 4-hydroxy-2-trichloromethylpyrimidine compound can be carried out by reacting the 4-hydroxy-2-trichloromethylpyrimidine compound with a selected carboxylic acid chloride in the presence of a base such as triethylamine, pyridine, sodium carbonate or potassium carbonate. Advantageously and preferably, the reactions are performed with at least a molar

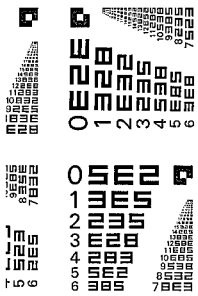

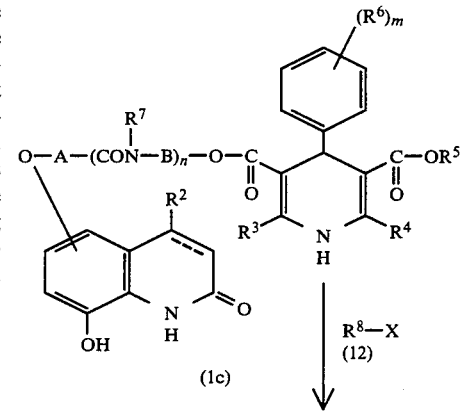

8 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful

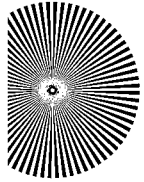

6 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful $$\cos \beta^* = \cfrac{K_2 - n\dfrac{T'}{v'}}{\sqrt{K_1^2 + \left(K_2 - n\dfrac{T'}{v'}\right)^2}} + K_3^2$$

4 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful $$v'_{ref}(t) = K r \delta \left( t - \frac{2L - 2d_s}{v_w} \right) + K (1 - r^2)e^{-2\alpha_s d_s}$$

8 PT. are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful 6 PT. Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful 4 PT. Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful $$(K_1 x + K_2 y + K_3 z + T) + n(K''_1 x + K''_2 y + K''_3 z + T'') = 0$$

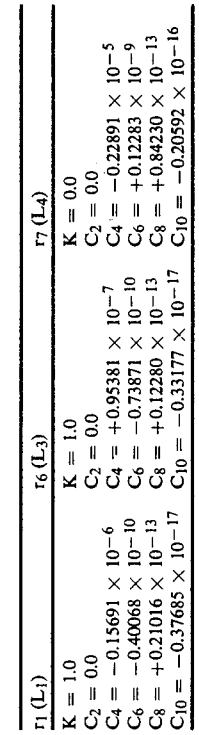

100mm

| = 101.2 | Aperture ratio: | 1:1.10 |  |  |
|---|---|---|---|---|
| agnification of projection: |  | $-7.997^x$ |  |  |
| lf angle of view: |  | 28.56° |  |  |
| 43.454 | $d_1 = 11.0$ | $n_1 = 1.49380$ | $L_1$ |  |
| -1542.254 | $d_2 = 68$ |  |  |  |
| 16.976 | $d_3 = 20.0$ | $n_2 = 1.62286$ | $L_2$ |  |
| 10.914 | $d_4 = 2.87$ |  |  |  |
| -89.375 | $d_5 = 5.0$ | $n_3 = 1.59501$ | $L_3$ |  |
| -127.071 | $d_6 = 58.8$ |  |  |  |
| -48.609 | $d_7 = 5$ | $n_4 = 1.49380$ | $L_4$ |  |
|  | $d_8 = 5$ | $n_5 = 1.45000$ | S |  |
| ∞ | $d_9 = 8$ | $n_6 = 1.51872$ | G |  |

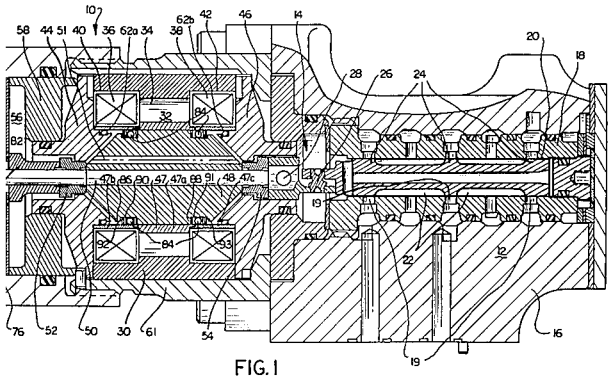

FIG.1

IMAGE SYSTEM
TEST TARGET
A
U.S. DEPARTMENT OF COMMERCE
PATENT AND TRADEMARK OFFICE

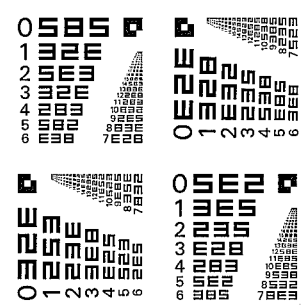

EXAMPLE 1

Preparation of 5-Chloro-4-Hydroxy-6-Methyl-2-Trichloromethylpyrimidine

A mixture of 30.0 g (0.18 mole) trichloroacetamidine, 25.2 g (0.18 mole) potassium carbonate, 30.3 g (0.18 mole) ethyl 2-chloroacetoacetate, and 300 ml water was stirred 18 hours. The aqueous solution was decanted from heavier tars and acidified with hydrochloric acid. The precipitate that was formed was filtered, washed, and dried to give 14.7 g (31% yield; mp 130°–145° C.) of crude product. An analytical sample was prepared by recrystallization from cyclohexane (mp 156°–157° C.). The structure was confirmed via infrared and elemental analysis.

Analysis for $C_6H_4N_2Cl_4O$:

|  | C | H | N | Cl |
|---|---|---|---|---|
| Calculated: | 27.51 | 1.54 | 10.74 | 54.15 |
| Found: | 28.20 | 1.88 | 11.00 | 52.54 |

EXAMPLE 2

Preparation of 5-Chloro-4-(2-Fluorobenzoxy)-6-Methyl-2-Trichloromethylpyrimidine A solution of 5.8 g (0.02 mole) 5-chloro-4-hydroxy-6-methyl-2-trichloromethylpyrimidine, 3.2 g (0.02 mole) 2-fluorobenzoyl chloride, and 2.0 g (0.02 mole) triethylamine in 100 ml diethyl ether was refluxed for 17 hours. After removal of triethylamine hydrochloride by filtration, the filtrate was concentrated in-vacuo to leave 8.4 g of residue, which, after recrystallization from ligroin, gave 4.6 g (59% yield) of pure product; m.p. 101° C.

Analysis for $C_{13}H_7Cl_4FN_2O_2$:

|  | C | H | N | Cl |
|---|---|---|---|---|
| Calculated: | 40.66 | 1.84 | 7.30 | 36.93 |
| Found: | 40.52 | 1.78 | 7.28 | 37.08 |

EXAMPLE 3

Preparation of 5-Chloro-6-Methyl-4-Trichloroacetoxy-2-Trichloromethylpyrimidine To a solution of 5.8 g (0.02 mole) 5-chloro-4-hydroxy-6-methyl-2-trichloromethylpyrimidine and 2.0 g (0.02 mole) triethylamine in 100 ml diethyl ether was added 3.6 g (0.02 mole) trichloroacetyl chloride. After the exothermic reaction subsided, the reaction mixture was stirred an additional 10 minutes and filtered. The filtrate was concentrated in-vacuo and the residue recrystallized from ligroin to give 1.6 g starting material and 2.3 g product; m.p. 92° C. The corrected yield was 35%.

Analysis for $C_8H_3Cl_7N_2O_2$:

|  | C | H | N |
|---|---|---|---|
| Calculated: | 23.59 | 0.74 | 6.88 |
| Found: | 22.39 | 1.05 | 7.02 |

EXAMPLE 4

Preparation of 4-Hydroxy-6-Methyl-2-Trichloromethylpyrimidine

A mixture of 44.4 g (0.28 mole) trichloroacetamidine, 32.0 g (0.28 mole) methyl acetoacetate, 37.5 g (0.28 mole) potassium carbonate, and 450 ml water was stirred for 3 days. A trace of solid was removed by filtration and the filtrate was made acidic with hydrochloric acid. The product precipitated out to give 28.9 g (46% yield; mp 173°–174° C.). The structure was confirmed via mp*, infrared, and elemental analysis.

*J. Med. Chem., 11, 608 (1968).

Analysis for $C_6H_5N_2Cl_3O$:

|  | C | H | N | Cl |
|---|---|---|---|---|
| Calculated: | 31.68 | 2.22 | 12.32 | 46.76 |
| Found: | 31.37 | 2.26 | 12.31 | 46.86 |

EXAMPLE 5

Preparation of 4-Crotonoxy-6-Methyl-2-Trichloromethylpyrimidine

To a solution of 3.0 g (0.02 mole) 4-hydroxy-6-methyl-2-trichloromethylpyrimidine and 1.3 g (0.02 mole) triethylamine in 75 ml diethyl ether was added 1.4 g (0.02 mole) crotonyl chloride. The reaction mixture was refluxed for 15 hours and filtered, and the filtrate was concentrated in-vacuo to give a viscous oil as residue. Trituration with petroleum ether caused the oil to solidify. Recrystallization from isopropyl alcohol gave 1.8 g (45% yield) of pure product; m.p. 55° C.

Analysis for $C_{10}H_9Cl_3N_2O_2$:

|  | C | H | N | Cl |
|---|---|---|---|---|
| Calculated: | 40.64 | 3.07 | 9.48 | 36.27 |
| Found: | 40.36 | 3.22 | 9.64 | 35.99 |

Foliar Fungicide Screen

The active materials formed in Examples 2, 3, and 5 were tested for activity as effective fungicides.

A uniform aqueous dispersion of each chemical made in the above examples was first prepared. These dispersions were made by dissolving each chemical in a solution of acetone containing the surfactant TRITON X-155[1] (concentration 500 parts per million). Next, this solution was diluted with water (1:9) to obtain a stock solution of 10% by volume acetone and 90% by volume water with 50 ppm TRITON X-155 and the best chemical contained therein. This stock solution was diluted further with water/acetone mix to provide the desired concentration of the test material, if required.

[1]Manufactured by Rohm and Haas of Philadelphia, Pennsylvania and is a polyether alcohol.

The aqueous solutions containing each chemical were applied to various plants according to the methods stated below. These tests were designed to evaluate the ability of the chemical to protect non-infected foliage and eradicate recently established infection against major types of fungi such as anthracnose and mildew that attack above-ground parts of plants.

Cucumber Anthracnose

Two week old cucumber plants were sprayed while rotating the plants on a turntable with an aqueous solution that contained 260 parts per million by weight of the active chemicals of Examples 2, 3, and 5. Simultaneously, the soil in each pot was drenched with an aqueous dispersion of each chemical in the amount of 25 lb/acre. After the spray deposit had dried, the plants were atomized with a suspension of cucumber anthracnose spores (*Collectotrichum lagenarium*) and placed in a moist chamber at 70° F. for 24 hours. After 5 days in a greenhouse, the severity of pustule formation was rated on a scale of 0 (no inhibition) to 10 (complete inhibition). Subsequent tests were conducted as described, except that the materials were tested for control at lower dosages and the drench and spray applications were done separately. See Table I for the results of these tests.

TABLE I

| | FUNGICIDAL ACTIVITY AGAINST CUCUMBER ANTHRACNOSE | | | | | | | |
|---|---|---|---|---|---|---|---|---|
| Compound | 25 lb/acre drench & 260 ppm spray | 12.5 lb/acre drench | 6.3 lb/acre drench | 130 ppm spray | 65 ppm spray | 33 ppm spray | 16 ppm spray | 8 ppm spray |
| Example 2 | — | 5 | 0 | 10 | 8 | 4 | — | — |
| Example 3 | — | — | 2 | 8 | 9 | 8 | 2 | 2 |
| Example 5 | 10 | — | — | — | — | — | — | — |

Downey Mildew

Soybean plants were sprayed with solutions of the active chemicals of Examples 2, 3, and 5 at 260 ppm by weight and simultaneously the soil drenched with the chemical at 25 lb/acre. Lower concentrations, if examined, were tested separately as a spray at 130 and 65 ppm, and as a drench at 12.5 lb/acre. After the spray deposit had dried, the plants were atomized with a suspension of *Peronospora manshurica* and placed in a moist chamber at 65° F. for 1 day. After 5 days in a greenhouse, the severity of infection was rated on a scale of 0 (no inhibition) to 10 (complete inhibition). See Table II for the results of these tests.

TABLE II

| | FUNGICIDAL ACTIVITY AGAINST DOWNEY MILDEW | | | |
|---|---|---|---|---|
| Compound | 25 lb/acre drench & 260 ppm spray | 12.5 lb/acre drench | 130 ppm spray | 65 ppm spray |
| Example 2 | 5 | — | — | — |
| Example 3 | 10 | 8 | 5 | 2 |
| Example 5 | 10 | — | — | — |

What is claimed is:

1. A compound having the formula:

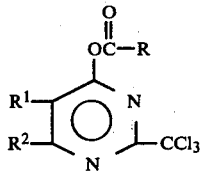

wherein R is a lower alkyl group having 1 to 4 carbon atoms, a lower alkenyl group having 1 to 4 carbon atoms, a lower halo alkyl group having 1 to 4 carbon atoms or an unsubstituted or substituted phenyl group; $R^1$ is hydrogen or halo; and $R^2$ is a lower alkyl group having 1 to 4 carboj atoms.

2. The compound of claim 1 wherein R is a lower alkyl group having 1 to 4 carbon atoms.
3. The compound of claim 2 wherein $R^1$ is hydrogen.
4. The compound of claim 2 wherein $R^1$ is halo.
5. The compound of claim 1 wherein R is a lower alkenyl group having 1 to 4 carbon atoms.
6. The compound of claim 5 wherein $R^1$ is halo.
7. The compound of claim 5 wherein $R^1$ is halo.
8. The compound of claim 1 wherein R is a lower halo alkyl group having 1 to 4 carbon atoms.
9. The compound of claim 8 wherein $R^1$ is hydrogen.
10. The compound of claim 8 wherein $R^1$ is halo.
11. The compound of claim 1 wherein R is an unsubstituted phenyl group.
12. The compound of claim 11 wherein $R^1$ is hydrogen.
13. The compound of claim 11 wherein $R^1$ is halo.
14. The compound of claim 1 wherein R is a substituted phenyl group.
15. The compound of claim 14 wherein $R^1$ is hydrogen.
16. The compound of claim 14 wherein $R^1$ is halo.
17. A method of controlling fungi which comprises contacting said fungi with a fungicidally effective amount of a compound having the formula:

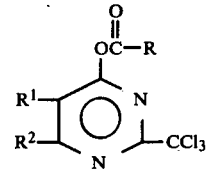

wherein R is a lower alkyl group having 1 to 4 carbon atoms, a lower alkenyl group having 1 to 4 carbon atoms, a lower halo alkyl group having 1 to 4 carbon atoms or an unsubstituted or substituted phenyl group; $R^1$ is hydrogen or halo; and $R^2$ is a lower alkyl group having 1 to 4 carbon atoms.
18. The method of claim 17 wherein R is a lower alkenyl group having 1 to 4 carbon atoms.
19. The method of claim 18 wherein said compound is 4-crotonoxy-6-methyl-2-trichloromethylpyrimidine.
20. The method of claim 17 wherein R is a lower halo alkyl group having 1 to 4 carbon atoms.
21. The method of claim 20 wherein said compound is 5-chloro-6-methyl-4-trichloroacetoxy-2-trichloromethylpyrimidine.
22. The method of claim 17 wherein R is a substituted phenyl group.
23. The method of claim 22 wherein said compound is 5-chloro-4-(2-fluorobenzoxy)-6-methyl-2-trichloromethylpyrimidine.

* * * * *

UNITED STATES PATENT AND TRADEMARK OFFICE
CERTIFICATE OF CORRECTION

PATENT NO. : 4,352,806

DATED : October 5, 1982

INVENTOR(S) : Lawrence E. Katz, Walter A. Gay

It is certified that error appears in the above-identified patent and that said Letters Patent is hereby corrected as shown below:

In Column 3, lines 29 and 30, delete "5-chloro-4-(2-fluorobenzoxl)-6-methyl-2-trichloromethylpyrimidine" and insert --5-chloro-4-(2-fluorobenzoyl)-6-methyl-2-trichloromethylpyrimidine--.

In Column 6, line 53, delete "best" and insert --test--.

In Column 7, line 65, Claim 1, delete "carboj" and insert --carbon--.

In Column 8, line 7, Claim 6, delete "halo" and insert --hydrogen--.

Signed and Sealed this

Eighteenth Day of January 1983

[SEAL]

Attest:

GERALD J. MOSSINGHOFF

Attesting Officer

Commissioner of Patents and Trademarks